United States Patent [19]

Linhart et al.

[11] 3,960,903

[45] June 1, 1976

[54] PROCESS FOR PREPARING 1-NITRO-ANTHRAQUINONE

[75] Inventors: Karl Linhart, Leverkusen; Reinold Schmitz, Blecher, both of Germany

[73] Assignee: Bayer Aktiengesellschaft, Leverkusen, Germany

[22] Filed: Aug. 27, 1974

[21] Appl. No.: 501,017

[30] Foreign Application Priority Data
Sept. 5, 1973   Germany............................ 2344736

[52] U.S. Cl. ............................................. 260/369
[51] Int. Cl.² ......................................... C07C 49/68
[58] Field of Search .................................... 260/369

[56] References Cited
UNITED STATES PATENTS
1,845,281   2/1932   Jaeger................................. 260/369

Primary Examiner—Arthur P. Demers
Attorney, Agent, or Firm—Burgess, Dinklage & Sprung

[57] ABSTRACT

1-Nitro-anthraquinone is separated from an anthraquinone nitration mixture in concentrated nitric acid by adding to the nitration mixture sulpholan and separating off the insoluble 1-nitro-anthraquinone. The quantity of sulpholan added is such that the mixture contains 10–90% by weight nitric acid and from 90–10% by weight sulpholan.

10 Claims, No Drawings

PROCESS FOR PREPARING 1-NITRO-ANTHRAQUINONE

BACKGROUND

This invention relates to a process for separating 1-nitro-anthraquinone from an anthraquinone nitration mixture in concentrated nitric acid.

Anthraquinone can be nitrated in sulphuric acid, phosphoric acid, hydrofluoric acid and nitric acid to form 1-nitro-anthraquinone. In all these media, and especially in nitric acid, 2-nitro-anthraquinones and dinitro-anthraquinones are produced in addetion to the desired 1-nitro-anthraquinone (see N. S. Dokunichin and Z. Z. Moiseeva, Z. vses. chim. Obsc. 11, 35 (1966); Houben-Weyl, Methoden der organischen Chemie Volume 10/1, 614 (1971)). Various methods have been proposed for separating or purifying 1-nitro-anthraquinone, e.g. the treatment of crude 1-nitro-anthraquinone with acid amides according to German Auslegeschrift No. 2 039 822; treatment with halogenated alkanes according to German Offenlegungsschrift No. 2 142 100; treatment with aqueous solutions of sodium sulphite according to U.S. Pat. No. 2 302 729; or the recrystallisation from suitable solvents, for example from glacial acetic acid, and finally distillation according to German Patent Specification No. 281 490. In all these methods, the removal of anthraquinone and 1,5-dinitro-anthraquinone at the same time gives rise to difficulties.

SUMMARY

It has now been found that very pure 1-nitro-anthraquinone can easily be obtained by adding sulpholan to anthraquinone nitration mixtures in concentrated nitric acid, especially those mixtures which contain 1-nitro-anthraquinone as their main component, and then separating the insoluble 1-nitro-anthraquinone.

DESCRIPTION

Particularly suitable anthraquinone nitration mixtures are those which have been obtained by nitrating anthraquinone in nitric acid, preferably pure, highly concentrated nitric acid, which may contain up to 10 % by weight, based on the total weight of the mixture, of nitration activators such as Lewis acids or sulphuric acid. The preparation of such anthraquinone nitration mixtures has been described, for example, in German Offenlegungsschriften Nos. 2 162 538, 2 220 337, 2 227 340 and 2 252 013.

The separation of 1-nitro-anthraquinone according to the invention is carried out from nitration mixtures which preferably contain from 10–90% by weight, more preferably from 30–70% by weight of nitric acid at a concentration of preferably 80–99%, more preferably above 90%, and preferably from 90–10 % by weight, more preferably from 30–70% by weight, of sulpholan, at temperatures of preferably from −10° to 100°C, more preferably from 20° to 40°C, preferably using molar ratios of nitric acid to anthraquinone products of from 5:1 to 120:1, in particular from 15:1 to 60:1.

The optimum quantity of sulpholan depends on the temperature, on the nitric acid concentration and on the proportion of anthraquinone products present. By anthraquinone products are meant the total quantity of anthraquinone compounds (unreacted antraquinone, 1-nitro-anthraquinone, 2-nitro-anthraquinone and dinitro-anthraquinones.

The process according to the invention for preparing 1-nitro-anthraquinone may be carried out continuously or discontinuously. The continuous process may be carried out by continuously nitrating anthraquinone in conventional manner to the desired degree of conversion in highly concentrated nitric acid, preferably higher than 90 % nitric acid, and then adding sulpholan to the nitration mixture, separating the insoluble 1-nitro-anthraquinone, recovering nitric acid having a concentration higher than 90% from the mother liquor by distillation and re-using it for the nitration of anthraquinone.

Nitration is carried out in conventional manner either continuously or discontinuously, for example at temperatures of from −40° to 75°C, preferably from −10° to 35°C, using nitric acid at a concentration of at least 90 % and a molar ratio of nitric acid to anthraquinone of up to 200:1 and preferably between about 10:1 and 50:1, the reaction being carried out either isothermally or adiabatically. The temperature and concentration of nitric acid and the molar ratio of nitric acid to anthraquinone influence the reaction time and total yield. The reaction time may be from 5 to 20 minutes, for example. Nitration is suitably controlled to result in about 50–100 % conversion, preferably 70–96 % conversion.

The sulpholan is preferably added at temperatures of from about −10° to 60°C when the desired degree of nitration has been reached. After the addition of sulpholan, part of the nitric acid is preferably distilled off and the precipitated 1-nitro-anthraquinone is then separated, preferably at temperatures of from 0°–50°C, washed with sulpholan and then with water, and then dried.

Alternatively, part of the sulpholan may be added when the desired degree of nitration has been reached, and concentrated nitric acid may then be distilled off, followed by addition of the remaining sulpholan before the precipitated 1-nitro-anthraquinone is removed.

According to another variation, nitration is stopped when the desired degree of conversion has been reached, for example by adding nitration inhibitors of the kind described in German Offenlegungsschrift No. 2 227 340 or by adding water or dilute nitric acid (see DOS No. 2 220 377) and only then is the desired quantity of sulpholan added and the product worked up as indicated above.

1-Nitro-anthraquinone is a known, important intermediate product for dyes, and for this purpose it must be used in a very pure state.

In the examples, the percentages are by weight and temperatures are in degrees centigrade unless otherwise indicated.

EXAMPLE 1

21 g of anthraquinone are introduced into 200 ml of 98 % $HNO_3$ at −10° and the reaction mixture is stirred for 38 minutes at −10°. 125 ml of sulpholan are then added, the temperature rising to 18° as a result of this. 173 ml of 98 % $HNO_3$ are distilled off at 35°/10 mm. The resulting precipitate is suction-filtered, and washed with sulpholan and then with water until neutral. After drying, 13.6 g of 1-nitro-anthraquinone, which is shown by analysis to have the following composition, is obtained:

96.3 % of 1-nitro-anthraquinone, 1.1 % of 1,5-dinitro-anthraquinone,
0.8 % of 1,8-dinitro-anthraquinone, 0.7 % of 2-nitroantraquinone,
1.4 % of anthraquinone, and
1.5 % unidentified products.

The yield is 52 % of the theoretical amount.

If the same procedure is repeated, except that the reaction mixture is diluted with only 100 ml of sulpholan and 140 ml of 98 % nitric acid are distilled off, then 16.3 g of 96.4 % 1-nitro-anthraquinone are obtained. The yield is then 61.5 % of the theoretical amount.

EXAMPLE 2

21 g of anthraquinone are introduced into 100 ml of 98 % HNO$_3$ at 20° and the mixture is stirred at this temperature for 8 minutes. 50 ml of sulpholan are then added, the temperature rising to 53°. 40 ml of 98 % HNO$_3$ are distilled off at 35°/10 mm, a further 50 ml of sulpholan are added, the reaction mixture is filtered at 40° and the precipitate is washed with a small quantity of sulpholan and then with water. After drying, 13.9 g of 1-nitro-anthraquinone are obtained, having the following composition:
  95.8 % 1-nitro-anthraquinone,
  1.2 % 1,5-dinitro-anthraquinone,
  1.2 % 1,8-dinitro-anthraquinone,
  0.3 % 1,6-dinitro-anthraquinone,
  0.3 % 1,7-dinitro-anthraquinone,
  1.1 % 2-nitro-anthraquinone, and
  0.9 % anthraquinone.

The yield is 52.7 % of the theoretical amount.

EXAMPLE 3

42 g of anthraquinone are added to 200 ml of 98 % nitric acid at 20° and 100 ml of sulpholan are added to the reaction mixture after 9 minutes. 80 ml of 98 % nitric acid (35°/10 mm) are distilled off. The reaction mixture is heated to 102°, the precipitate being thereby dissolved. It is then cooled to 40° and filtered at this temperature, washed twice with 20 ml portions of a mixture of 10 parts of HNO$_3$ and 1 part of sulpholan, and then washed with water until neutral. 29.2 g of 1-nitro-anthraquinone which is found when analysed to have the following composition, are obtained:
  94.2 % of 1-nitro-anthraquinone,
  1.6 % of 1,8-dinitro-anthraquinone,
  1.4 % of 1,5-dinitro-anthraquinone,
  0.8 % of 2-nitro-anthraquinone, and
  2.0 % of anthraquinone.

The yield is 54.3 % of the theoretical amount.

19.7 of nitro-anthraquinones, found by analysis to have the following composition, can be obtained from the mother liquor and washing liquids:
  47.5 % of 1-nitro-anthraquinone,
  3.8 % of 1,5-dinitro-anthraquinone,
  3.8 % of 1,8-dinitro-anthraquinone,
  0.9 % of 1,7-dinitro-anthraquinone,
  0.9 % of 1,6-dinitro-anthraquinone,
  15.2 % of 2-nitro-anthraquinone, and
  28.9 % of anthraquinone.

EXAMPLE 4

20 g of anthraquinone are introduced into 100 ml of 98 % HNO$_3$ at 0°, the temperature rising to 10° in two minutes as a result of this addition. The reaction mixture is then nitrated at 10° for 20 minutes, with cooling by iced water. 100 ml of sulpholan are added, the temperature rising to 50° as a result. The reaction mixture is suction-filtered at 20° and the precipitate is washed with 50 ml of sulpholan and then with water, and dried. 12.7 g of 1-nitro-anthraquinone, formed by analysis to have the following composition, are obtained:
  95 % of 1-nitro-anthraquinone,
  0.9 % of 2-nitro-anthraquinone,
  1.3 % of 1,5-dinitro-anthraquinone,
  1.1 % of 1,8-dinitro-anthraquinone, and
  approximately 2 % of anthraquinone.

The yield is 49.6 % of the theoretical amount.

10 g of nitro-anthraquinones, formed by analysis to have the following composition, can be obtained from the mother liquor and washing liquids:
  56.5 % of 1-nitro-anthraquinone,
  0.9 % of 2-nitro-anthraquinone,
  4.8 % of 1,5-dinitro-anthraquinone,
  4.4 % of 1,8-dinitro-anthraquinone,
  0.6 % of 1,6-dinitro-anthraquinone,
  0.6 % of 1,7-dinitro-anthraquinone, and
  25.7 % of anthraquinone.

What is claimed is:

1. Process for separating 1-nitro-anthraquinone from an anthraquinone nitration mixture in concentrated nitric acid which comprises adding sulpholan to the nitration mixture and separating the insoluble 1-nitro-anthraquinone.

2. Process of claim 1 wherein the nitration mixture contains from 30 to 70% by weight of nitric acid.

3. Process of claim 1 wherein the nitric acid has a concentration of above 90%.

4. Process of claim 1 wherein separation is carried out at a temperature of from −10° to 100°C.

5. Process of claim 4 wherein the temperature is from 20° to 40°C.

6. Process of claim 1 wherein the nitration mixture has a molar ratio of nitric acid to anthraquinone products of from 5 : 1 to 120 : 1.

7. Process of claim 6 wherein the molar ratio is from 15 : 1 to 60 : 1.

8. Process of claim 1 wherein the quantity of sulpholan added is such that the mixture contains from 10 to 90% by weight of nitric acid and from 90 to 10% by weight of sulpholan.

9. Process of claim 8 wherein the mixture contains from 30 to 70% by weight of nitric acid and from 70 to 30% by weight of sulpholan.

10. Process for the continuous preparation of 1-nitro-anthraquinone which comprises nitrating anthraquinone in concentrated nitric acid, adding sulpholan to the nitration mixture when the desired degree of nitration has been reached, distilling off higher than 90% nitric acid after separation of the 1-nitro-anthraquinone and returning the distilled nitric acid to the nitration reaction mixture.

* * * * *